United States Patent [19]

Nishibe et al.

[11] Patent Number: 5,155,241

[45] Date of Patent: Oct. 13, 1992

[54] PROCESS FOR PREPARING STYRENE OXIDE

[75] Inventors: Keiichi Nishibe, Takaoka; Seiichi Rengakuji; Masami Inoue, both of Toyama; Osami Ohura; Hirohisa Nitoh, both of Fuji, all of Japan

[73] Assignee: Tokai Denka Kogyo Kabushiki Kaisha, Tokyo, Japan

[21] Appl. No.: 772,556

[22] Filed: Oct. 7, 1991

[30] Foreign Application Priority Data

Oct. 5, 1990 [JP] Japan .................. 2-266420

[51] Int. Cl.$^5$ .......................... C07D 301/12
[52] U.S. Cl. .................................. 549/531
[58] Field of Search ........................ 549/531

[56] References Cited

U.S. PATENT DOCUMENTS

| 2,431,718 | 12/1947 | Wilder et al. | 549/531 |
| 3,806,467 | 4/1974 | Watanabe et al. | 549/531 |
| 4,418,203 | 11/1983 | Kim | 549/531 |
| 5,041,569 | 8/1991 | Enomoto et al. | 549/531 |

FOREIGN PATENT DOCUMENTS 3602254  7/1987  Fed. Rep. of Germany ...... 549/531

*Primary Examiner*—J. E. Evans
*Attorney, Agent, or Firm*—Scully, Scott, Murphy & Presser

[57] ABSTRACT

Styrene oxide is prepared by reacting styrene and hydrogen peroxide in a heterogenous system in the presence of a bis(tri-n-alkyltinoxy) molybdic acid and an inorganic anion.

6 Claims, No Drawings

PROCESS FOR PREPARING STYRENE OXIDE

BACKGROUND OF THE INVENTION

The present invention relates to a process of preparing styrene oxide by the reaction of styrene and hydrogen peroxide in the presence of a catalyst.

Styrene oxide is used over a wide range of field, for example as a stabilizer for polymers, an ultraviolet ray absorber, a starting material in the preparation of drugs, a stabilizer for solvents, or as a starting material for phenethyl alcohol and phenethyl aldehyde which are useful as synthetic perfumes and sweetening materials.

For preparing styrene oxide by the epoxidation of styrene there generally is adopted a process in which styrene is epoxidized using an organic peracid, as described in Japanese Patent Laid Open No. 149271/1980. However, this process involves the following drawbacks and is not always satisfactory.

(1) During the reaction of oxidizing styrene with an organic peracid, the organic peracid is decomposed and there occurs an addition reaction of the resulting radical to styrene, thus resulting in that the selectivity of styrene oxide with respect to styrene is deteriorated.

(2) The resulting styrene oxide cleaves in the presence of an organic acid byproduced after the reaction, thereby producing an ester and a hydroxy compound, whereby the selectivity of styrene oxide with respect to styrene is deteriorated.

(3) Peracetic acid which is most easily available industrially among organic peracids is prepared by a so-called Daicel-Wacker process comprising air oxidation of acetaldehyde, but it is a very expensive oxidizing agent.

(4) In order to avoid a possible danger in the use of an organic peracid it is necessary to pay close attention to both operation and equipment.

On the other hand, an oxidation reaction using hydrogen peroxide byproduces only water and does not cause the problem of environmental pollution; besides, hydrogen peroxide is easily available industrially and is inexpensive. In principle, therefore, hydrogen peroxide is a desirable epoxidizing agent. In the preparation of an epoxide by the reaction of styrene and hydrogen peroxide, however, the styrene conversion and the selectivity to the epoxide are both low. The low conversion is because hydrogen peroxide remains unreacted in the reaction performed at a low temperature, while in the reaction performed at a high temperature hydrogen peroxide decomposes and produces oxygen, and thus hydrogen peroxide is not effectively consumed in reaction.

The reason why the selectivity to epoxide is low is that water which is introduced into the reaction system together with hydrogen peroxide and water resulting from the reaction both cause the formation of polyol.

The reactivity of styrene in epoxidation is as tabulated below (see "Encyclopedia of Polymer Science and Technology" Vol. VI (1967), Interscience Publishers, New York, p. 83). The epoxidizing speed of styrene is relatively low in comparison with other olefins; for example, it is about one tenth as compared with a relative reactivity in the epoxidation of cyclohexene, thus indicating that the epoxidation reaction rate of styrene is very low.

| Olefin | Relative Reactivity |
| --- | --- |
| $CH_2=CH_2$ | 1 |
| $C_6H_5CH_2-CH=CH_2$ | 11 |
| $R-CH=CH_2$ | 25 |
| $Ar-CH=CH-Ar$ | 27 |
| $Ar-CH=CH_2$ | 60 |
| $Ar-CH=CH-R$ | 240 |
| $(Ar)_2C=CH_2$ | 250 |
| $R-CH=CH-R$ | 500 |
| $(R)_2C=CH_2$ | 500 |
| Cyclohexene | 675 |
| Cycloheptene | 900 |
| Cyclopentene | 1000 |
| $(R)_2C=CH-R$ | 6500 |
| $(R)_2C=CH(R)_2$ | >>6500 |

In the above table, Ar and R represent aryl and alkyl, respectively.

In order to solve the above-mentioned problems involved in the preparation of styrene oxide by the reaction of styrene and hydrogen peroxide, there has heretofore been proposed the use of a specific catalyst.

For example, according to J. Org. Chem., 53, 1553, (1988), styrene oxide is obtained in 74% yield (based on hydrogen peroxide) if a quaternary ammonium salt of phosphotungstic acid is used as a hydrogen peroxide epoxidizing catalyst. Although this reported process is greatly improved in the yield of styrene oxide as compared with other conventional processes, it is difficult to adopt it on an industrial scale because the quaternary ammonium salt (an interphase transfer catalyst) used as a catalyst component is every expensive.

In Japanese Patent Laid Open No. 129276/1980 there is proposed a process wherein styrene and hydrogen peroxide are reacted in the presence of arsenic oxide and 3,5-di-tertbutyl-4-hydroxytoluene. However, a combined use of arsenic oxide with aqueous hydrogen peroxide involves such drawbacks as rapid decomposition of hydrogen peroxide and a low epoxidizing speed. Further, since arsenic compounds are strong in toxicity, it is necessary to pay close attention to the manufacturing equipment to prevent poisoning during production and also during use of the resulting products with the arsenic compounds incorporated therein.

In U.S. Pat. No. 3,806,467 there is proposed a process wherein an olefin and hydrogen peroxide are reacted in the presence of a bis(tri-n-methyltinoxy)molybdic acid catalyst to prepare an epoxide. However, as long as the working Examples thereof are reviewed, the yield of styrene oxide is a little lower than 3% (based on hydrogen peroxide) and thus this proposed process cannot be considered preferable as a styrene oxide preparing process although the yield of cyclohexene epoxide is high and the process in question is effective as a cyclohexene epoxide preparing process. It is presumed that the low yield of styrene oxide in the said process is because the resulting styrene oxide cleaves oxidatively and byproduces benzaldehyde and further benzoic acid.

The bis(tri-n-methyltinoxy)molybdic acid catalyst described in the above U.S. Pat. No. 3,806,467 is inexpensive and easily available industrially and can be fixed to active carbon and also to organic adsorbent resins, thus permitting the reaction to be carried out in a heterogeneous catalyst system and thereby permitting easy separation of the catalyst from the reaction system.

It is the object of the present invention to solve the above-mentioned problems of the process proposed in the foregoing U.S. Pat. No. 3,806,467 and provide an improved process capable of suppressing the formation of byproducts and affording styrene oxide in high yield under application of the process proposed in the said U.S. patent to the preparation of styrene oxide from styrene.

SUMMARY OF THE INVENTION

The present invention resides in a process of preparing, styrene oxide by the reaction of styrene and hydrogen peroxide in the presence of alkyltin oxide - molybdic acid catalyst, wherein an inorganic anion is made present as a promotor in the reaction and the reaction is carried out in a heterogeneous system.

The process of the present invention can afford the desired styrene oxide in high activity and high selectivity at a low temperature.

DETAILED DESCRIPTION OF THE INVENTION

The hydrogen peroxide used in the present invention may be a commonly-used one. An aqueous solution containing 5 to 90 wt % of hydrogen peroxide is employable, but it is desirable to use a 10–70 wt % aqueous solution thereof which is available easily.

In the reaction of styrene and hydrogen peroxide, both may be used in an equimolar amount. But either of the two may be used in a too small or too large amount.

For example, usually 0.1 to 3.0 moles of hydrogen peroxide is employable, but preferably 0.3 to 2.0 moles of hydrogen peroxide is used, per mole of styrene.

The alkyltin oxide - molybdic acid catalyst used in the present invention can be prepared easily by a known process. There may be used an addition product prepared from ammonium molybdate and alkyltin oxide which are catalyst components, or the catalyst components may be added separately into the reaction system and the reaction may be allowed to take place in situ.

As alkyltin oxides employable in the invention there are dialkyltin oxides and trialkyltin oxides. Preferred alkyl groups are those having 1 to 18 carbon atoms, particularly n-alkyl groups having 1 to 8 carbon atoms. Examples of such alkyltin oxides include di-n-methyltin oxide, di-n-ethyltin oxide, di-n-propyltin oxide, di-n-butyltin oxide, di-n-octyltin oxide, tri-n-memthyltin oxide, tri-n-ethyltin oxide, tri-n-propyltin oxide, tri-n-butyltin oxide, and tri-n-octyltin oxide.

The amount of the catalyst to be used is usually larger than 0.0001 mole, preferably larger than 0.001 mole. The upper limit thereof is not specially limited, but usually it is less than 0.1 mole, preferably less than 0.01 mole.

As examples of the inorganic anion used as a promotor there are mentioned sulfate ion and nitrate ion. The amount of the inorganic anion is usually in the range of 0.1 to 6.0 moles, preferably 0.3 to 2.0 moles, per mole of the molybdic acid catalyst. The inorganic anion can be foremed by the addition of a salt thereof, e.g. sodium sulfate, sodium nitrate, or potassium sulfate.

The epoxidation reaction in the present invention is conducted in a heterogeneous system, which is formed using an organic solvent immiscible with water. More particularly, the starting styrene and styrene oxide as an oxidation product are present in a dissolved state in the water-immiscible organic solvent, while hydrogen peroxide is present in the aqueous phase, and thus there are formed two phases which are the organic solvent phase and the aqueous phase.

By using an organic solvent immisible with water it is made possible to avoid the contact between styrene oxide as an oxidation product and water.

The organic solvent employable in the invention is not specially limited if only it is inert to the reaction and immiscible with water. Examples thereof include monochloromethane, dichloromethane, chloroform, carbon tetrachloride, dichloroethane, trichloroethane, tetrachloroethane, dichloroethylene, trichloroethylene, tetrachloroethylene, monochlorobenzene, dichlorobenzene, benzene, toluene, xylene, and mesitylene.

The reaction can be performed at a relatively low temperature because the catalyst used in the present invention is very high in activity as compared with conventional catalysts. The reaction temperature is usually in the range of 0° to 70° C., preferably 10° to 40° C.

The following examples are given to illustrate the present invention in more detail, but the invention is not limited thereto at all.

EXAMPLE 1

5 ml (43.7 mmol) of styrene, 5 ml of monochloromethane, 0.07 mmol of ammonium molybdate $[(NH_4)_6MO_7 \cdot 4H_2O]$, 1 mmol of di-n-octyltin oxide and 0.6 mmol of sodium sulfate were charged into an Erlenmeyer flask having a capacity of 50 ml, then stirred together with 1 ml of water at room temperature for 20 minutes. After the ammonium molybdate and the di-n-octyltin oxide had been dissolved, 3 ml (43.7 mmol) of 60% hydrogen peroxide was added at a time, followed by immersion in a constant temperature bath with shaking apparatus held at 29°–30° C., and reaction was allowed to proceed for 24 hours.

Styrene and styrene oxide were analyzed by gas chromatographyy, while the amount of residual hydrogen peroxide was determined by iodometric titration. The results obtained are as shown in Table 1.

EXAMPLE 2

Reaction was performed in the same way as in Example 1 except that 0.6 mmol of sodium nitrate was used in place of sodium sulfate. The results obtained are as shown in Table 1.

COMPARATIVE EXAMPLE-1

Reaction was performed in the same way as in Example-1 except that there was used no inorganic anion. The results obtained are as set forth in Table 1.

TABLE 1

| | (on hydrogen peroxide basis) | | |
| --- | --- | --- | --- |
| | Conversion | Yield | Selectivity |
| Comparative Example-1 | 77% | 34% | 45% |
| Comparative Example-1 | 69% | 59% | 86% |
| Comparative Example-2 | 62% | 62% | 100% |

What is claimed is:

1. A process for preparing styrene oxide which comprises reacting styrene and hydrogen peroxide in the presence of an alkyltin oxide-molybdic acid catalyst, characterized in that the reaction is carried out in a heterogeneous system in the presence of an inorganic anion.

2. A process as set forth in claim 1, wherein the alkyltin oxide-molybdic acid is a bis(tri-n-alkyltinoxy) molybdic acid.

3. A process as set forth in claim 1, wherein the heterogenous system comprises water and an organic solvent immiscible with water, the styrene and styrene oxide being soluble the solvent.

4. A process as set forth in claim 1, wherein the inorganic anion is sulfate anion or nitrate anion.

5. A process as set forth in claim 1, wherein the amount of the inorganic anion is in the range of 0.1 to 6.0 moles per mole of the alkyltin oxide-molybdic acid catalyst.

6. A process as set forth in claim 1, wherein the reaction is carried out at a temperature in the range of 0° C. to 70° C.

* * * * *